United States Patent
Birch et al.

(10) Patent No.: US 7,455,852 B2
(45) Date of Patent: Nov. 25, 2008

(54) INSECT REPELLENTS

(75) Inventors: Richard Arthur Birch, Hyth (GB); Henk Helweg, Huizen (NL)

(73) Assignee: Quest International B.V., Naarden (NL)

( * ) Notice: Subject to any disclaimer, the term of this patent is extended or adjusted under 35 U.S.C. 154(b) by 871 days.

(21) Appl. No.: 10/486,423

(22) PCT Filed: Jul. 23, 2002

(86) PCT No.: PCT/GB02/03369

§ 371 (c)(1),
(2), (4) Date: Feb. 10, 2004

(87) PCT Pub. No.: WO03/013243

PCT Pub. Date: Feb. 20, 2003

(65) Prior Publication Data
US 2004/0213822 A1    Oct. 28, 2004

(30) Foreign Application Priority Data
Aug. 11, 2001   (GB) .......................... 0119660.9

(51) Int. Cl.
*A01N 25/32*    (2006.01)
(52) U.S. Cl. .................. 424/406; 514/919; 514/729; 514/763; 514/764; 514/739; 514/533
(58) Field of Classification Search ............... None
See application file for complete search history.

(56) References Cited

U.S. PATENT DOCUMENTS 5,227,163 A * 7/1993 Eini et al. .................... 514/546
5,439,690 A * 8/1995 Knight ........................ 424/687
6,001,874 A * 12/1999 Veierov ...................... 514/533
6,974,584 B2 * 12/2005 Bessette ...................... 424/406

FOREIGN PATENT DOCUMENTS

| EP | 0 619 363 A | 10/1994 |
| EP | 000619363 A1 * | 10/1994 |
| WO | WO 00/27197 | 5/2000 |

OTHER PUBLICATIONS

Derwent Publication Ltd., London, GB; AN 1990-118678 XP002212228 IWASE COSFA: :Insect repellent resin mouldings—contains inorganic porous microcapsules enclosing repellent core abstract & JP 02 067202 A Mar. 7, 1990.
Chemical Abstracts Service, Columbus, Ohio, US; Inazuka, Shinichi et al: "Monoterpenoids as cockroach repellent" retrieved from STN Database accession No. 90:17693 XP002212226 abstract & JP 53 086021 A (AJINOMOTO Co., Inc., Japan) Jul. 29, 1978.
Chemical Abstracts Service, Columbus, Ohio, US; Verma, M. et al.: "A natural cockroach repellent in bay leaves" retrieved from STN Database accession No. 95:199004 XP002212227 abstract & Am. Lab. (Fairfield, Conn.) (1981), 13(10), 64, 66-9.

* cited by examiner

*Primary Examiner*—Neil Levy
(74) *Attorney, Agent, or Firm*—Morgan Lewis Bockius LLP

(57) ABSTRACT

The present invention provides an insect repellent fragrance comprising; (a) at least 10% by weight of the insect repellent fragrance of geraniol; (b) at least 10% by weight of the insect repellent fragrance of diethyl phthalate; and (c) at least one or more of linalol, limonene, citronellal, terpinolene and p-tertiary butyl cyclohexyl acetate; wherein the insect repellent fragrance comprises at least 60% by total weight of the insect repellent fragrance of (a), (b) and (c). The insect repellent fragrance surprisingly demonstrates effective repellency, particularly against cockroaches, and more particularly against both German and American cockroaches.

8 Claims, 1 Drawing Sheet

INSECT REPELLENTS

FIELD OF THE INVENTION

Figure 1:
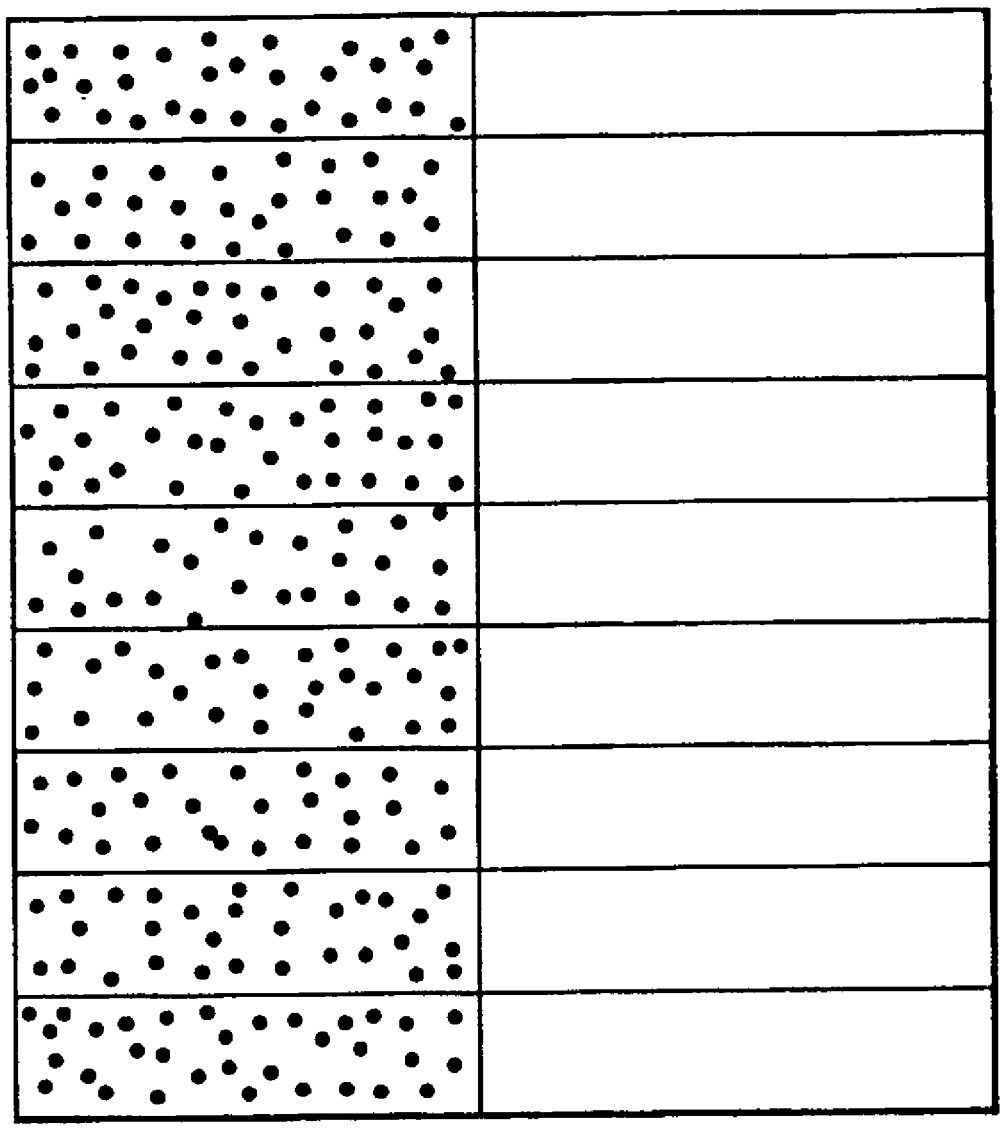

The present invention relates to fragrances, particularly insect repellent fragrances, to products comprising such fragrances and to a method of repelling insects.

BACKGROUND OF THE INVENTION

Insects have long been known to be a nuisance to humans, and for some insect genera, a health hazard.

Many common types of household insects such as cockroaches, e.g. American cockroaches (*periplaneta americana*) and German cockroaches (*blattella germanica*), are classified as pests and significant effort has been made to control or eradicate them. A variety of chemical compounds have been discovered, e.g. N,N-diethyl-meta-toluamide, which are efficacious in repelling cockroaches. Such chemical compounds are used in the household by applying or spraying them to surfaces of walls, floors, cabinets, containers, rugs, upholstery and carpeting, and in potential nesting places for these insects, such as inside walls and between floors. Chemical compounds have been used together with hard surface cleaners (EP-A-0619363) and wax floor polishes (U.S. Pat. No. 3,018,217).

It is known in the art that essential oils and synthetic fragrance ingredients (also known as perfume materials) can repel insects. Further, use of these ingredients may be advantageous compared with the use of chemical compounds in terms of presenting lower toxicity to mammals. WO 96/08147 describes an insect repellent composition comprising at least one active ingredient from the group of compounds consisting of: 1,2,3a,4,5,5a,6,7,8,9,9a,9b-dodecahydro-3a,6,6,9a-tetramethylnaphtho [2,1-b] furan (AMBERLYN™); 4-(tricyclo [$5.2.1.0^{2.6}$] decylidene-8) butanal (DUPICAL™); 1-ethoxy-1-(2'-phenylethoxy) ethane (EFETAAL™); acetyl cedrene (LIXITONE™); and propylidene phthalide. The compositions are described as preferably used to repel biting insects, such as mosquitoes, and in particular members of the genus *Aedes*.

Perfume materials, or fragrances, with repellent properties to either American cockroaches (*periplaneta americana*) e.g. as disclosed in WO 00/19822 and Ngoh S. P. et al., *Pestic. Sci.*, 1998, 54, p261, or German cockroaches (*blattella germanica*) e.g. as disclosed in JP 2207004, are known. However, typically, it is difficult to formulate a complete fragrance which effectively repels cockroaches, particularly German cockroaches, and more particularly, repels both German and American cockroaches, possibly together with other crawling insects e.g. ants.

SUMMARY OF THE INVENTION

In one aspect, the present invention provides an insect repellent fragrance comprising;
(a) at least 10% by weight of the insect repellent fragrance of geraniol;
(b) at least 10% by weight of the insect repellent fragrance of diethyl phthalate; and
(c) at least one or more of linalol, limonene, citronellal, terpinolene and p-tertiary butyl cyclohexyl acetate;

wherein the insect repellent fragrance comprises at least 60% by total weight of the insect repellent fragrance of (a), (b) and (c).

The present invention is based on the appreciation that insect repellent fragrances of the invention surprisingly demonstrate effective repellency against cockroaches, particularly German cockroaches (*blattella germanica*), and more particularly against both German and American cockroaches (*blattella germanica* and *periplaneta americana*).

By "insect repellent fragrance" as used herein is meant a fragrance comprising the specified fragrance ingredients generally (but not necessarily) having an odour that is considered pleasant or attractive, and which has an insect repellent effect. One convenient procedure by which the insect repellent effect can be tested and measured involves incorporating the insect repellent fragrance into a liquid polish, with 3.0 ml of the liquid polish being evenly applied to half the area (i.e. 300 mm×600 mm) of a vinyl flooring test surface of total area 600 mm×600 mm, which is then divided into nine channels (30 mm×600 mm) so that half of each channel (30 mm×600 mm) is treated and half is untreated, the liquid polish being allowed to dry for approximately one hour before at least five insects are introduced into each channel and allowed to acclimatise to the conditions for about ten minutes, after which, i.e. at t=0 hours, the movements of the insects are measured by video recorder. An insect repellent fragrance initially, i.e. at t=1 hour, preferably repels from the treated area at least 60%, more preferably at least 65%, most preferably at least 70%, of the insects.

The term "insect" as used herein is intended to encompass insects which typically crawl e.g. cockroaches such as German cockroaches (*blattella germanica*) and American cockroaches (*periplaneta americana*) as well as ants e.g. from the genera *lasius flavus, lasius niger* and *monomorium pharoanis*. Preferably, fragrances in accordance with the present invention are used to repel cockroaches, particularly German cockroaches and more particularly both German and American cockroaches.

Typically, the insect repellent fragrance comprises at least one or more of linalol, limonene, citronellal, terpinolene and p-tertiary butyl cyclohexyl acetate (PtBCHA), preferably at least two, more preferably at least three, and even more preferably at least four of these fragrance ingredients. Conveniently, when present, insect repellent fragrances as defined herein comprise at least 1% linalol, at least 2% limonene, at least 2% and preferably greater than 3% citronellal, at least 2% and preferably greater than 3% terpinolene, and at least 3% p-tertiary butyl cyclohexyl acetate by weight of the insect repellent fragrance.

The insect repellent fragrance may optionally be admixed with further excipients such as one or more further fragrance ingredients to obtain an overall pleasing fragrance with effective repellent activity, diluents, fixatives, and a further suitable solvent, or mixtures thereof.

Other excipients which may advantageously be present in the insect repellent fragrances in accordance with the invention are: aldehyde C11 (undecylenic aldehyde); aldehyde iso C11 (GIV); allspice oil; allyl cyclohexyl propionate; amyl salicylate; amylcinnamic aldehyde; anethole; anisic alcohol; anisic aldehyde; Applinal (Q) (Applinal is a Trade Mark); bay oil; benzyl acetate; benzyl benzoate; benzyl cinnamate; benzyl propionate; benzyl salicylate; Bourgeonal (Q) (Bourgeonal is a Trade Mark); brahmanol; camphor powder synthetic; cedarwood Virginian; cedrenol; cedryl acetate; Celestolide (IFF) (Celestolide is a Trade Mark); cineole; cinnamic alcohol; cinnamic aldehyde; cinnamon leaf oil; cinnamyl acetate; cis-3-hexenol; citral; citronella oil; citronellol; citronellyl acetate; citronellyl oxyacetaldehyde; clove oil; coriander oil; coumarin; cuminic aldehyde; cyclamen aldehyde; decanal; 9-decenol; dibenzyl ether; dibutyl phthalate;

dihydromyrcenol; dimethyl anthranilate; dimethyl phthalate; Dimycretol (IFF) (Dimycretol is a Trade Mark); diphenyl methane; diphenyl oxide; dimethyl benzyl carbinyl acetate; dodecanol; dodecanal; elemi oil; ethyl methyl phenyl glycidate; ethyl cinnamate; Ethyl Safranate (Q) (Ethyl Safranate is a Trade Mark); ethyl vanillin; eugenol; evergreen oils (pine oils etc.); gamma-nonalactone; gamma-undecalactone; geranium bourbon; geranyl acetate; geranyl formate; gum benzoin; heliotropin; Hercolyn D (HER) (Hercolyn D is a Trade Mark); hexyl benzoate; hexylcinnamic aldehyde; hexyl salicylate; hydratropic aldehyde dimethyl acetal; hydroxycitronellal; hydroxycitronellal dimethyl acetal; indole; iso bornyl acetate; isopropyl myristate; iso-cyclocitral (GIV, IFF); jasmacyclene; jasmin oil; lavandin abrialis; lavender oil; Lilial (GIV) (Lilial is a Trade Mark); linalyl acetate; menthol laevo; methyl anthranilate; methyl cedryl ketone; methyl dihydrojasmonate; methyl ionone; methyl myristate; methyl naphthyl ketone; methyl salicylate; moss treemoss; musk ketone; nerol; nerolin bromelia; neryl acetate; nonanal; oakmoss absolute; octanal olibanum resinoid; para-cresyl phenylacetate; para-methoxyacetophenone; patchouli oil; peppermint oil; petitgrain oil; 2-phenoxyethanol; phenoxyethyl iso butyrate; phenylethylacetate; phenyethyl alcohol; phenylethyl butyrate; phenylethyl phenylacetate; pimento oil; pinene, alpha; resinoid benzoin siam; rose oil; rosemary oil; sandalwood oil; terpineol; tetrahydrolinalol; Tetrahydromuguol (IFF); thyme red; undecanal; vanillin; verbena oil; vetyvert bourbon; yara and ylang ylang.

Compounds are obtainable from the suppliers as indicated below: for those compounds labelled "(Q)",—Quest International; "(IFF)"—International Flavours & Fragrances, Inc.; "(GIV)"—Givaudan; "(HER)"—Hercules B.V.

The insect repellent fragrance may optionally include other known insect repellents, and preferably known insect repellent fragrance ingredients.

Suitable known insect repellents for use herein include N,N-diethyl-m-toluamide (DEET); N,N-diethylbenzamide; citronella; Tolu balsam; Peru balsam; Eucalyptus oil; Huon pine oil; camphor; cypress oil; galbanum; dibutyl phthalate; dimethyl phthalate; 1,2,3a,4,5,5a,6,7,8,9,9a,9b-dodecahydro-3a,6,6,9a-tetramethylnaphtho[2,1-b] furan; 4-(tricyclo [5.2.1.0$^{2,6}$]decylidene-8) butanal; 1-ethoxy-1-(2'-phenylethoxy)ethane; acetyl cedrene; propylidene phthalide; citral diethyl acetal available under the trade mark "CITRATHAL"; tricyclodecenyl allyl ether available under the trade mark "FLEUROXENE"; 2-(2-methylpropyl)-4-hydroxy-4-methyltetrahydropyran available under the trade mark "FLOROSA"; N-methyl-N-phenyl-2-methylbutanamide available under the trade mark "GARDAMIDE", 4-isobutyrate-3-methoxybenzaldehyde available under the trade mark "ISOBUTAVAN"; 1-hydroxy-2-methoxy-4-propenyl benzene; 2,2,7,7-tetramethyltricyclo[6.2.1.0$^{1,6}$]undecan-5-one available under the trade mark "ISOLONGIFOLANONE"; 7-formyl-5-isopropyl-2-methylbicyclo(2.2.2)oct-2-ene available under the trade mark "MACEAL"; 3-methyl-5-phenylpentanal available under the trade mark "MEFRANAL"; alpha iso methyl ionone; myrcenyl acetate available under the trade mark "NEOBERGAMATE"; 10-isopropyl-2,7-dimethyloxaspiro [4.5] 3,6-decadiene available under the trade mark "NEOCASPIRENE"; tricyclo [5.2.1.0$^{2,6}$]dec-4-en-8-yl 2,2-dimethylpropanoate available under the trade mark "PIVACYCLENE"; 2-phenylethyl pivalate available under the trade mark "PIVAROSE" and 2,4-dimethyl-4-phenyltetrahydrofuran available under the trade mark "RHUBAFURAN".

Insect repellent fragrances in accordance with the invention are preferably incorporated in products for application to a surface e.g. floors, walls, counters, sinks, cupboards, furniture or doors etc.. The invention in a further aspect therefore provides a product comprising an insect repellent fragrance in accordance with the invention.

Suitable and preferred products include for example, hard surface cleaners, pastes and polishes e.g. furniture polish, floor polish and floor paste in typically liquid or solid e.g. wax form. A particularly preferred product is a floor polish.

Preferably, the products defined herein above comprise between 0.01% to 20% and more preferably 0.1% to 10% by weight of the product of an insect repellent fragrance in accordance with the present invention.

In an even further aspect, the invention provides a product comprising an insect repellent fragrance, wherein the product comprises;
(a) at least 0.025% by weight of the product of geraniol;
(b) at least 0.025% by weight of the product of diethyl phthalate; and
(c) at least one or more of linalol, limonene, citronellal, terpinolene and p-tertiary butyl cyclohexyl acetate; and wherein the product comprises at least 0.15% by total weight of the product of (a), (b) and (c).

The product will typically comprise further suitable adjuvants appropriate to the nature of the product. Suitable adjuvants may include wax e.g. paraffin, carnauba, ceresin wax etc., resins, plasticizers, water, surfactants e.g. anionic, cationic, nonionic, amphoteric compounds, builders, fluorescent brighteners, antistatic agents, antibacterial agents, fungicides, foaming agents, anti-foams, flow promoters, suspending agents, and anti-gelling agents.

Insect repellent fragrances according to the present invention in their simplest form as a fragrance, or as part of a product, may be applied to a surface, including floors, furniture, walls etc. by spraying, for instance as an aerosol or by a pump action, by brushing, by wiping, for instance from an impregnated cloth or with an applicator, pouring etc. on the surface to be treated.

Thus, in an even further aspect, the invention provides a method of repelling insects from a surface comprising the step of applying to the surface an effective amount, typically from 0.001 to 1.000 g/m$^2$, of an insect repellent fragrance, preferably a product comprising from 0.01% to 20% by weight of the product of an insect repellent fragrance, in accordance with the present invention.

In an even further aspect the invention provides the use of an insect repellent fragrance in accordance with the present invention for repelling cockroaches, particularly German cockroaches (*blattella germanica*) and/or American cockroaches (*periplaneta americana*).

The invention is illustrated by way of the following non-limiting examples, and with reference to the accompanying drawing, in which:

FIG. 1 is a schematic representation of the arrangement of a test area used to determine the repellency of a fragrance to insects of interest, the test area being divided into nine equal channels, with half of the total area treated with a fragrance (as shown by the spotted shading) and half untreated.

EXAMPLES

The repellency of fragrances in accordance with the present invention, particularly to German cockroaches (*blattella germanica*) and American cockroaches (*periplaneta americana*), was demonstrated as described below. For comparison, fragrances not in accordance with the present invention were also prepared and tested using the same protocol.

Fragrances 1 to 4 in accordance with the present invention, and comparative fragrances 5 to 7, were prepared in the proportions indicated in the table below. All percentages are by weight.

| Ingredient | Frag. 1 | Frag. 2 | Frag. 3 | Frag. 4 | Frag. 5 | Frag. 6 | Frag. 7 |
|---|---|---|---|---|---|---|---|
| Citronellal | 4 | 6 | 12 |  | 2 |  |  |
| Geraniol | 24 | 36 | 12 | 12 |  |  |  |
| Terpinolene | 4 | 6 | 12 |  |  | 2 |  |
| Diethyl phthalate | 20 | 16 | 16 | 20 | 20 | 20 | 20 |
| Benzyl acetate | 5 | 5 | 5 | 5 | 6 | 5 | 5 |
| Hexyl salicylate | 5 | 3 | 3 | 3 | 3 | 3 | 3 |
| Lavandin | 10 | 10 | 10 | 6 | 9 | 6 | 6 |
| Linalol | 5 | 5 | 5 | 4 | 4 | 5 | 4 |
| Methyl dihydrojasmonate | 3 | 3 | 5 | 2 | 2 | 3 | 2 |
| Terpineol | 5 | 4 | 6 | 5 | 5 | 5 | 5 |
| Iso bornyl acetate | 4 | 3 | 5 | 9 | 9 | 11 | 12 |
| Limonene | 5 | 3 | 5 | 15 | 15 | 16 | 18 |
| Cedarwood Virginian | 1 |  |  | 4 | 5 | 4 | 5 |
| PtBCHA | 3 |  | 3 | 10 | 15 | 15 | 15 |
| Diphenyl methane | 2 |  | 1 | 5 | 5 | 5 | 5 |
| Total | 100 | 100 | 100 | 100 | 100 | 100 | 100 |

The fragrances prepared were then incorporated into a self-shining liquid floor polish i.e. a floor polish which dries with a shiny finish and does not typically require buffing, the formulation of which is indicated below:

| Ingredient | % w/w |
|---|---|
| Hoescht-Wachs (Hoescht) | 10.20 |
| Demineralised water (boiling) | 20.40 |
| Demineralised water (room temperature) | 63.70 |
| Licomer A53 conc. (Hoescht) (acrylate polymer) | 4.50 |
| Bronidox L (Henkel) (5-bromo-5-nitro-1,3 dioxane) | 0.20 |
| Lutensol ON70 (BASF) (Synthetic C10 oxo-alcohol with 7 ethylene oxide units) | 0.50 |
| Fragrances 1 to 7 | 0.50 |

LICOMER, BRONIDOX and LUTENSOL are all trade marks.

Each self-shining liquid floor polish comprising one of fragrances 1 to 7 was tested for its ability to repel German cockroaches (*blattella germanica*) and American cockroaches (*periplaneta americana*) according to the following protocol.

Each fragrance was tested against each species of cockroach, with one species of cockroach used per test.

The test surface was vinyl flooring of 600 mm×600 mm total area which was divided into an arena of nine equally sized channels each of 30 mm×600 mm, as illustrated in FIG. 1. 3.0 ml of a polish was applied by syringe to the test surface and the polish distributed evenly with an applicator such that half of the total test surface area (300 mm×600 mm) was treated with the polish, as represented by the spotted area in FIG. 1, and half the total test surface area was untreated. The polish was left to dry for approximately one hour. Five cockroaches, *periplaneta americana* or *blattella germanica,* of mixed age and gender were placed in each channel and their behaviour monitored by video recorder. The video recording commenced 10 minutes after introduction of the cockroaches to the channels and was stopped after 1 hour of recording. The cockroaches were then removed. After 24 hours, five cockroaches were returned to each of the channels and the recording process repeated. The video recording was played back and stopped at five minute intervals over an hour to obtain twelve readings. At each five minute interval, the number of cockroaches on the treated area was counted. The repellency for the nine channels was calculated as follows:

Total number of cockroach observations possible=540 (12 times, 9 channels, 5 insects per channel)

Total number of cockroach observations on treated area if no effect=540/2=270

Total number of cockroaches observed on treated area=N (total of 12 times for 9 channels)

Therefore, Repellency (%)=(270−N)/270×100

The results are as indicated in the table below with the number representing the percentage of cockroaches of a particular species repelled from the treated area.

| Fragrance | | t = 1 hour | t = 24 hours |
|---|---|---|---|
| 1 | *periplaneta americana* | 88 | 63 |
|  | *blattella germanica* | 94 | 52 |
| 2 | *periplaneta americana* | 71 | 69 |
|  | *blattella germanica* | 64 | 68 |
| 3 | *periplaneta americana* | 84 | 69 |
|  | *blattella germanica* | 79 | 86 |
| 4 | *periplaneta americana* | 85 | 74 |
|  | *blattella germanica* | 72 | 85 |
| 5 | *periplaneta americana* | 94 | 87 |
| (comparative) | *blattella germanica* | 57 | 61 |
| 6 | *periplaneta americana* | 97 | 78 |
| (comparative) | *blattella germanica* | 32 | 58 |
| 7 | *periplaneta americana* | 81 | −15 |
| (comparative) | *blattella germanica* | 59 | 2 |

The results show that only Fragrances 1, 2, 3 and 4 repel at least 60% of both species of cockroach (i.e. *periplaneta americana* and *blattella germanica*) initially. Whilst comparative fragrances 5 and 6 demonstrate effective repellency to cockroaches of the species *periplaneta americana*, they demonstrate poorer repellency to the *blattella germanica* species. Comparative fragrance 7 does not demonstrate effective repellency against either species of cockroach after 24 hours.

The invention claimed is:

1. An insect repellent fragrance comprising:
   (a) at least 10% by weight of the insect repellent fragrance of geraniol;
   (b) at least 10% by weight of the insect repellent fragrance of diethyl phthalate; and
   (c) the insect repellant fragrance of at least one or more of linalol, limonene, citronellal, terpinolene and p-tertiary butyl cyclohexyl acetate provided that the fragrance comprises at least 2% by weight of the insect repellant fragrance of terpinolene; and
   wherein the insect repellent fragrance comprises at least 60% by total weight of the insect repellent fragrance of (a), (b) and (c).

2. An insect repellent fragrance according to claim 1, wherein the fragrance comprises at least two of linalol, limonene, citronellal, and p-tertiary butyl cyciohexyl acetate.

3. An insect repellent fragrance according to claim 1 or 2, wherein the fragrance comprises at least 1% by weight of the insect repellent fragrance of linalol.

4. An insect repellent fragrance according to claim 1 or 2, wherein the fragrance comprises at least 2% by weight of the insect repellent fragrance of limonene.

5. An insect repellent fragrance according to claim 1 or 2, wherein the fragrance comprises at least 2% by weight of the insect repellent fragrance of citronellal.

6. An insect repellent fragrance according to claim 1 or 2, wherein the fragrance comprises at least 3% by weight of the insect repellent fragrance of p-tertiary butyl cyclohexyl acetate.

7. A method of repelling cockroaches selected from the group consisting of German cockroaches (*blattella germanica*) and American cockroaches (*periplaneta americana*) which comprises subjecting said cockroaches to an effective amount of a fragrance according to claim 1 or 2.

8. The method of claim 7 wherein the insect repellent fragrance includes, as (c), each of linalol, limonene, citronellal, terpinolene and p-tertiary butyl cyclohexyl acetate.

* * * * *